(12) United States Patent
Badgett

(10) Patent No.: US 6,904,914 B2
(45) Date of Patent: Jun. 14, 2005

(54) PENISSTER SYSTEM

(75) Inventor: Henry O. Badgett, 3447 E. 115th Dr., Thornton, CO (US) 80233

(73) Assignee: Henry O. Badgett, Thornton, CO (US)

( * ) Notice: Subject to any disclaimer, the term of this patent is extended or adjusted under 35 U.S.C. 154(b) by 0 days.

(21) Appl. No.: 10/147,209

(22) Filed: May 16, 2002

(65) Prior Publication Data
US 2002/0134389 A1 Sep. 26, 2002

Related U.S. Application Data

(63) Continuation of application No. 09/599,170, filed on Jun. 22, 2000.

(51) Int. Cl.[7] ............................................. A61F 6/02
(52) U.S. Cl. .................... 128/842; 128/844; 602/918
(58) Field of Search ......................... 128/842, 844, 128/918; 604/347–353

(56) References Cited

U.S. PATENT DOCUMENTS

| | | | | |
|---|---|---|---|---|
| 1,229,423 A | * | 6/1917 | Eckenrode | 604/353 |
| 3,161,198 A | * | 12/1964 | Moxley | 604/353 |
| 4,790,834 A | * | 12/1988 | Austin | 604/349 |
| 5,009,649 A | * | 4/1991 | Goulter | 604/351 |
| 5,618,277 A | * | 4/1997 | Goulter | 604/349 |
| 5,746,730 A | * | 5/1998 | Suzuki | 604/385.2 |

* cited by examiner

Primary Examiner—Michael A. Brown

(57) ABSTRACT

The medical system 10 is an article of cloth, rubber and elastic made in the style of a pair of briefs, the front of the system 10 is made of a rubber material in the form of a shield 40 covered with cloth to protect direct contact from bodies of both partners in case of sexual activities. Attached to the shield 40 is namely a hollow tubal-shaped device 42 to be worn over the penis. The tubal-shaped device 42 has a nipple 53 at the end and can be used for sexual activities. The medical system 10 a pouch 56 beneath tubular-shaped device 42 to store device 42. Persons with prostate and bladder disorder may also use this medical system 10 for incontinence.

5 Claims, 5 Drawing Sheets

PENISSTER SYSTEM

CROSS-REFERENCE TO RELATED APPLICATIONS

This is a continuation of application Ser. No. 09/599,170, filed Jun. 22, 2000.

SPECIFICATION

A medical system made of a cloth, rubber and elastic material, with a hollowed tubal-shaped device to be worn over the penis with a nipple at the end of the member. Below the tubal-shaped member is a pouch for storing the device when not in use. The system also has an open and closed valve at the end of the member and is useful for persons with prostate, bladder disorders and other similar disorders. The system comes in an assortment of colors and also a number of sizes. This system promotes safe sexual activities and helps to prevent the spread of sexually transmitted diseases. The medical system has an elastic waistband, while the frame of the system is a polyester cloth. The system is made in the style of a pair of briefs and is re-usable indefinitely and maintained by using lukewarm water and a mild soap after every use.

STATEMENT REGARDING FEDERALLY SPONSORED RESEARCH FOR DEVELOPMENT

N/A

REFERENCE TO A MICROFICHE APPENDIX

N/A

BACKGROUND OF THE CREATION

In today's market, there are many products such as medicines, devices, diapers, pads, special designed briefs, clothing with attached devices (condoms) prophylactic systems, coital protective garments that are being offered for use in an effort to provide help with urology problems, safe sex, prostate, bladder dysfunction, AIDS and the spread of other sexually transmitted diseases. The prostate is a male sex gland that is important for reproduction in that it produces the majority of ejaculate fluid. It is a small walnut-shaped gland located above the rectum and at the bottom of the bladder. The prostate surrounds the urethra (the tube that carries urine from the bladder) like a doughnut, at the point where the urethra connects to the bladder. The prostate gland continues to grow throughout most of a man's life.

Prostate cancer cannot always be felt by a physician during a digital rectal exam; this is especially true in the earliest stage of the disease. Another barrier to early detection is the fact that signs and symptoms that could alert the individual to a possible problem may not occur until the disease has reached a more advanced stage. The prostate can "choke" the urethra causing a decreased force of the urinary stream, having to "push" the urine out feeling as if the bladder is not emptying, increased urinating during nighttime and intermittent stopping and starting of urine stream.

I had prostate surgery in 1992 and was told by physicians that if I had prostate problems after surgery, they had several treatment options. After I was in the stage for assistance with my first problem, I was truly amazed with the choices offered for my disorder. I was offered the latest available treatment on the market but I was never truly satisfied. I read a lot of material offered by Dr. Rums Green, Jr., M.D., FACS of RHD Memorial Medical Center, St. Paul Medical Center and Medical Center of Las Colins. After studying comprehensive diagnostics, education testing, research and treatments experienced by him, I decided to try and create a device I would be pleased with and to offer it as an assistance for others. It had to be a product that was safe, durable, reliable, useful, neat and something to present a new and comfortable solution in making prostate and bladder disorders easier to cope with on a daily basis. However, in order to be most effective, any such device must be easy to use when working, swimming, driving, at church, or when asleep. Any characteristics which are either restrictive or make the device difficult to use would vitiate it by discouraging use.

The bladder is a muscle. You may think of it as a small balloon. The bladder holds the urine produced by the kidneys. It expands to fill and contracts to empty. However, the bladder must work together with the sphincter muscle, which helps to hold the urine in the bladder. When urine is stored, the bladder is relaxed and the sphincter contracts to keep the urine inside the bladder. The system is controlled through the spinal cord and brain. When the bladder is full, the brain receives a message of discomfort. The brain, in turn, signals the bladder when there is an appropriate time to urinate or void. Voiding occurs by relaxing the sphincter muscle and contracting the bladder muscle. The urethra, a tube to the outside of the body, conducts the urine from the bladder. When any part of the system such as the bladder, spinal cord, or brain is not working properly, there may be leakage of urine.

When the decision is made to have prostate surgery, some of the consequences that can occur are impotence, indefinite light urine drainage, and drainage that enters the urethra channel. Bladder disorder and incontinence are a lack of bladder control or involuntary leakage. It is embarrassing and can even be painful. Bladder problems are common in men, even young men. Urine stress incontinence refers to the loss of urine due to any increase of pressure in the abdomen, such as laughing, sneezing or exercise. The most common clinical presentation for people with bladder cancer is blood in the urine or hematuria. Usually, this is painless and the blood may be visible to the naked eye (gross hematuria) or can be seen only under the microscope (microscopic hematuria). Frequently, the diagnosis of bladder cancer is delayed because bleeding is intermittent or attributed to other causes such as urinary tract infection or blood thinners. However, a substantial proportion of these patients will have a significant problem such as kidney stones or tumors, urinary tract obstruction and bladder cancer. Until now, people with poor bladder control had few choices if the medical profession was unable to correct their problem. In many cases, they were too embarrassed to consult with their doctor. Even the newer, disposable products leave a lot to be desired; they are uncomfortable and make the wearer extremely self-conscious and the cost over a year's time can be outrageous.

Sexual Activities

In recent times, there have been devices proposed for use in preventing the spread of sexually transmitted diseases, safe sex, pregnancy and AIDS. organ and protecting his partner from his secretion during intercourse, with the most common device being the condom. While such a sexual device is somewhat successful in the protection of pregnancy and helps in preventing the spread of certain diseases that are associated directly with contact between sexual partners, these devices are not totally successful in protecting against infection or the like of diseases that are spread due to general contact which can occur between partners in areas adjacent to the genitals. This system is a protective device affording a barrier protection to the genitals and surrounding skin area of the lower abdomen, pubic area and thighs as a means of precluding skin contact of each partner with the sexual body secretion of the other.

OBJECTS OF THE CREATION a. It is a medical system to assist people suffering from prostate and bladder dysfunctions.
b. It is a medical system for people with prostate and bladder disorders so they can choose the most comfortable size and color they desire.
c. It is a medical system that can be worn comfortably all day by persons with prostate and bladder disorders.
d. It is a medical system a person can choose for protective sex and choose the size and color he desires.
e. It is a medical system that can be worn with complete freedom as a pair of briefs.
f. It is a medical system that affords a barrier protection to the genitals and surrounding skin area of the lower abdomen, pubic area and thighs as a means of precluding skin contact of each partner with the sexual body secretion of the other.
g. It is a medical system that can be re-used indefinitely.
h. It is a medical system that can be maintained by washing with lukewarm water and a mild soap at the end of each day use.
i. It is a medical system that should never be used by more than one person.

BRIEF SUMMARY OF THE CREATION

These and other objects are achieved by an article of cloth, rubber and elastic that include a rubber shield-like element that covers the entire pubic area of the wearer. It also includes a tubal-shaped device that is worn over the penis. The system is sheath thereby making the insertion comfortable when wearing. The tubal-shaped device, the sheath-fitting of the rubber shield-like element ensures that the penis will remain securely in place even without an erection. The medical system is in an assortment of colors (brown, natural, pink) which is more pleasant for the wearer. The medical system also comes in three sizes. The medical tubal-shaped member has a nipple at the end of the device.

Wearers using the medical system for sexual purposes may wear the system as a pair of briefs. The system has a pouch located under the tubal-shaped device and the device may remain in the pouch until it is put into use. The medical system is a protective shield affording a barrier protection to genitals and surrounding skin area of the lower abdomen, pubic area and thighs as a means of precluding skin contact of each partner with the sexual body secretion of the other, to assist in the prevention and spread of sexually transmitted diseases.

DETAILED DESCRIPTION OF THE PREFERRED EMBODIMENT OF THE CREATION

Figure 3:
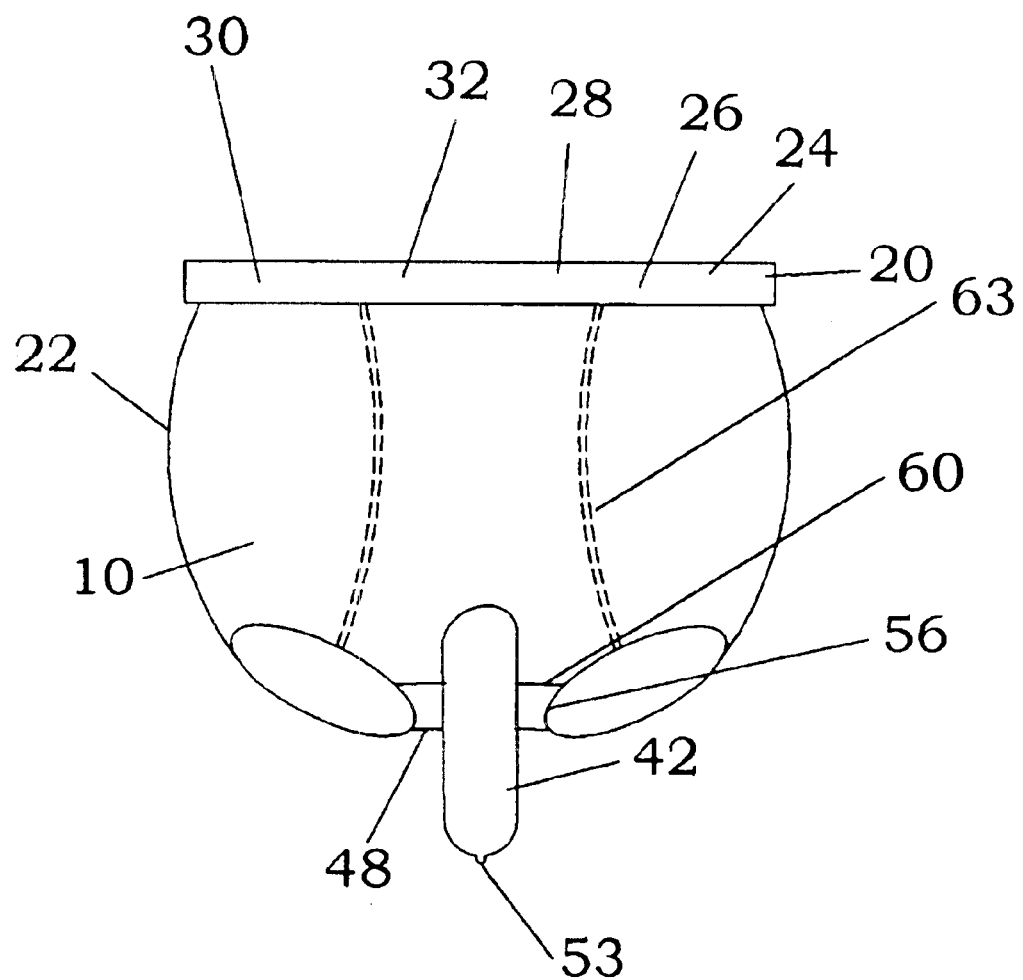
FIG. 3 is a perspective view showing the article of creation in display of conclusion of the medical system, all elements of structure, shield, pouch, tubal-shaped device, cloth, nipple at end of device, elastic encircling waistband, and stitched shield and cloth together.

The medical system 10 of the present creation is intended to provide enhanced service, protection and a more comfortable way for a person with prostate, bladder and other medical disorders to cope with his situation, intentions, or to elevate his stage of social awareness and decrease his level of frustration, anxiety, unnecessary shame and embarrassment by not having to be concerned if and when he experiences an uncontrollable bladder or prostate disorder. (refer to FIG. 3)

More specifically, the present creation of this medical system 10 can be a vital tool in sex activities such as safe sex, pregnancy and protection in transmittal of sexual diseases. The medical system 10 has an affording barrier protection that prevents the wearer and his partner from having direct contact in the area of the genitals and surrounding skin area of the lower abdomen and thighs as a means of precluding skin contact of each party with the sexual body secretion of the other.

Figure 1:
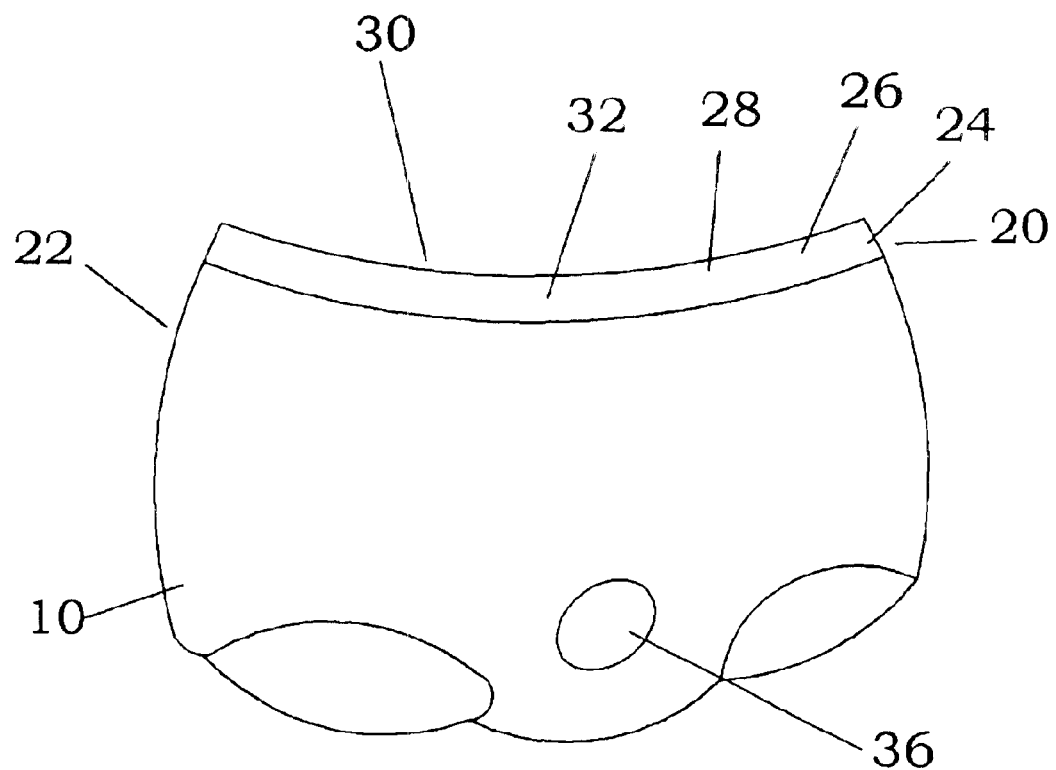
FIG. 1 is an exployed perspective showing the article of cloth and elastic encircling waistband embodying the present creation.
Figure 2:
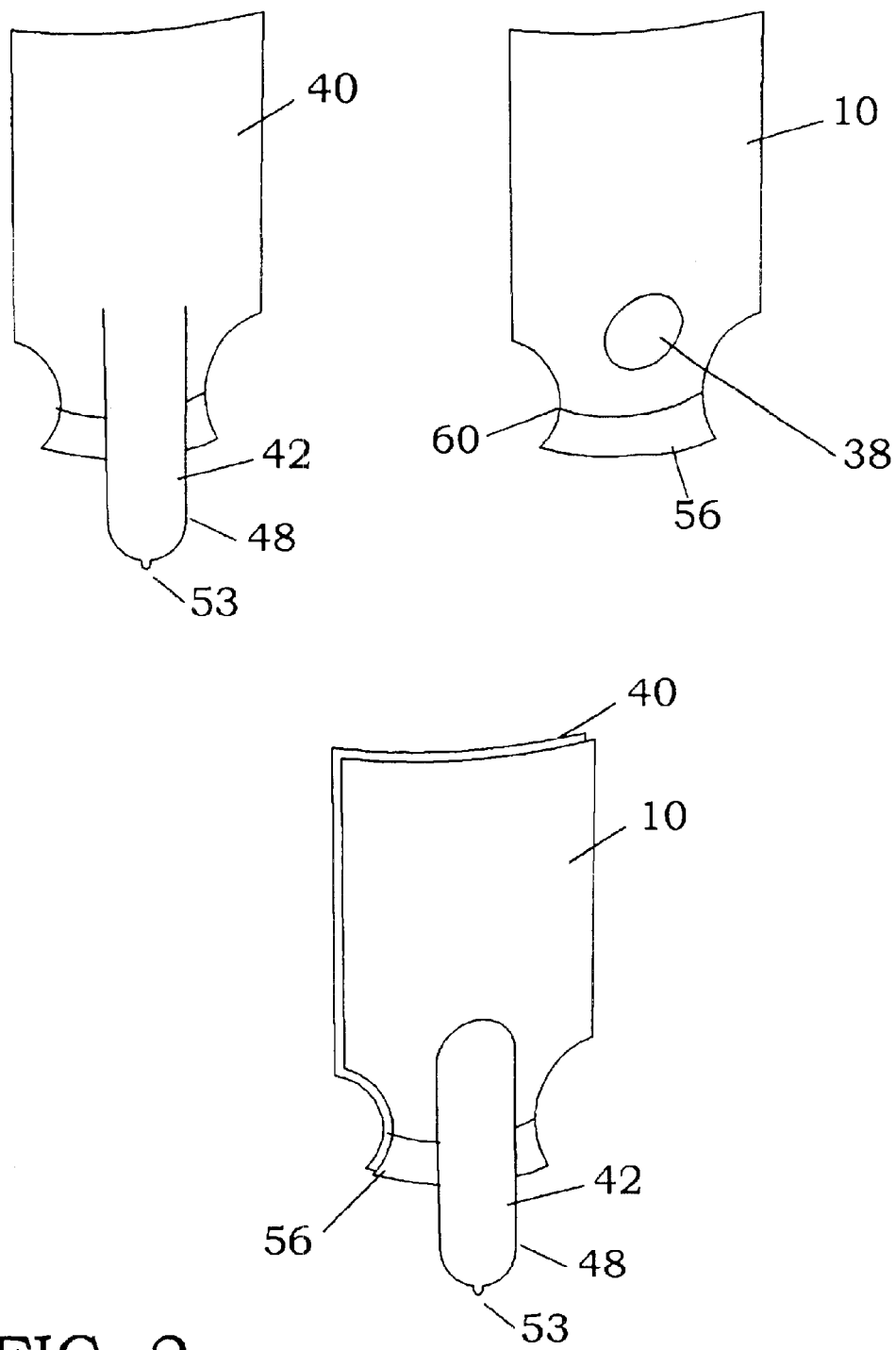
FIG. 2 is an exployed perspective showing the article of cloth and rubber embodying the present creation.
Figure 4:
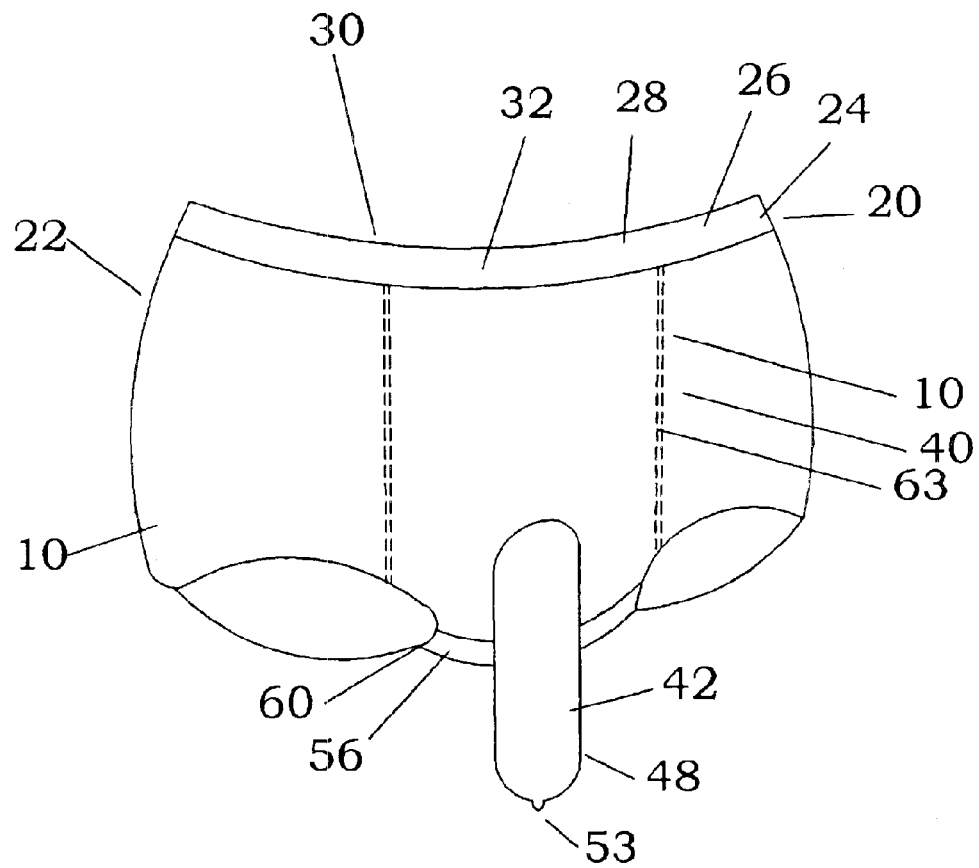
FIG. 4 is a perspective front view relative to article of creation FIG. 3 showing creation being used. Briefs, latex and top cloth layer assembled.

Shown in FIG. 1 is an article of cloth and an elastic encircling waistband 20 that circles the top of the medical system 10. The shield 40 is attached to the elastic encircling waistband at the top of the system. The cloth is 100% polyester and was chosen because it is a safe, durable, lightweight material, does not wrinkle and should be very comfortably worn as a pair of briefs. The polyester fabric is highly recommended to ensure its integrity, comfort and make it easier to wear and manufacture. Attached to the cloth is a special ordered elastic encircling waistband 20 that completely surrounds the wearer's waist when worn. In the ensuing disclosure, the various portions of the article of the system 10 will be described in terms that refer to the article in relation to the wearer when that article is worn. Accordingly, the article of the system 10 has an anterior portion 22 as well as a lateral portion 24 and 26 the waist encircling band 20 has an anterosuperior portion 28 that extends across the entire frontal portion of the wearer, and a posterosuperior portion 30 that extends across a portion of the rear area of the wearer's buttocks. Two portions such as portion 32 that connects the portion 28 and 26 together the elastic-encircling waistband 20 further connects posterosuperior of cloth portion 24 that extends partially across the rear of the wearer. The elastic encircling waistband 20 allows such elongation adjustments in the embodiment. The article of the elastic-encircling waistband 20 and the cloth in the rear of the system (see FIG. 1) further includes a shield-like element, 40 covers the front outside of the cloth and is sized and designed to cover the entire pubic area of the wearer. The shield 40 is preferably made of a latex rubber material with cloth to accommodate a lining between the shield 40 and the wearer's body; therefore, no part of the wearer's body comes in direct contact with the shield 40 which is one of the designed features. To prevent the spread of transmitted diseases associated with the pubic area, such as infestation of phthirus Inguinalis or any transmitted disease surrounding the skin area of genitals to include secretion from both partners. The article of cloth has an opening 36 in the front to allow direct entrance into the shield 40 that has an opening 38 cloth covers the shield 40 has an element like device 42 as part of the shield 40. The device 42 is tubul-shaped (Refer to FIG. 2). Cloth and shield 40 are attached to structure cloth. The tubul-shaped device 42 is used for sexual activities and by people with prostate, bladder and other medical disorders as a storage device. They wear this to avoid embarrassing moments when at work, at recreation facilities, at social gatherings or in an inconvenient situation with an uncontrollable bladder disorder, or any disorder that may cause uncontrollable discharge of a fluid. (refer to FIG. 4). This device 42 can also be used as a sex tool 48 for safe sex, pregnancy, and prevention of the spread of sexually transmitted diseases.

Figure 5:
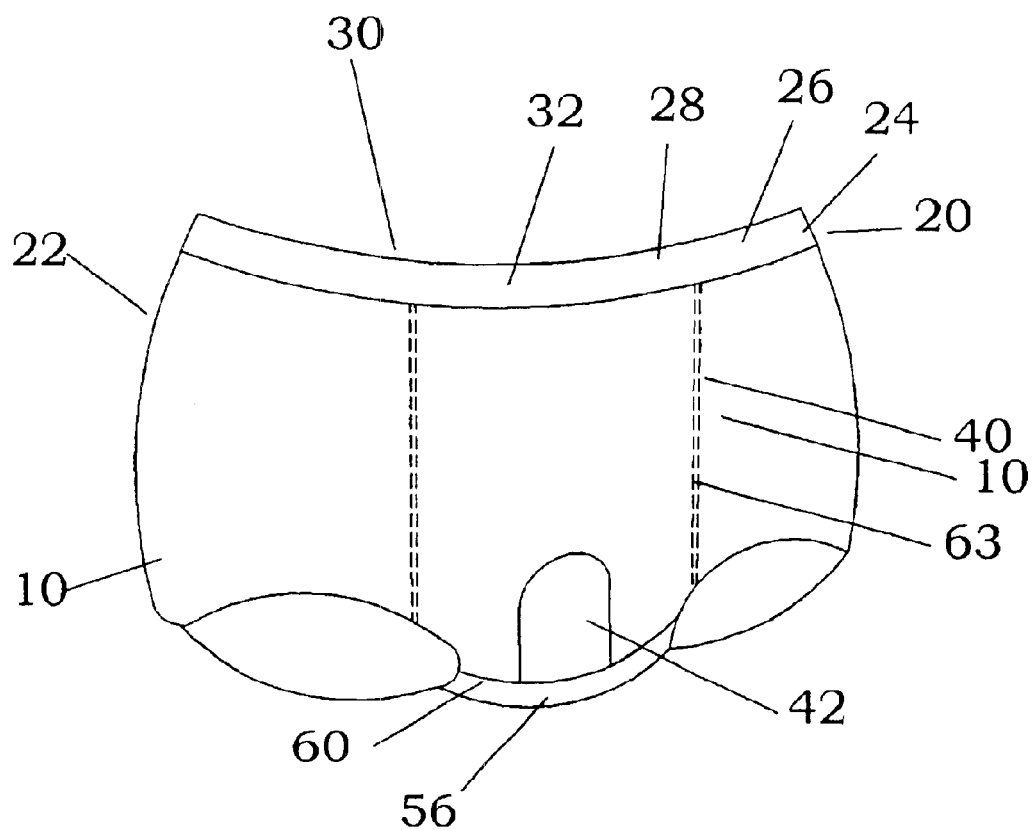
FIG. 5 is a perspective side view relative to article of creation FIG. 3 showing creation view of storing tubal-shaped device in pouch.

At the end of the device 42 is a nipple 53. The article of rubber shield 40 has another element the pouch 56 which is a part of the shield 40 the pouch 56 is located under the device 42 with an opening 60 at the top, it stores the device 42 when it is not in use.(Refer to FIG. 2) A person wearing the system 10 for sexual activities can wear it as a pair of briefs. When device 42 is needed, just remove from pouch (refer to FIG. 5). The article of rubber device 42, nipple 53 at end of device 42, pouch 56, opening 60, shield opening 38, cloth covering shield 40 are all stitched together (see FIG. 3).

What we claim is:

1. A medical system comprising a pair of briefs, said briefs are made of an elastic material and of an assortment of colors, said briefs having an opening therein, a shield made of rubber and cloth is attached to the front of said briefs, said shield having a hollow tubular-shaped device attached thereto, said hollow tubular shaped device having a nipple at its end, said medical system being different sizes to accommodate different size users, said briefs having an elastic waistband, said shield having a pouch to said briefs below said hollow tubular device in order to store said hollow tubular device therein, said elastic material being a polyester cloth.

2. The medical system of claim 1, wherein the briefs are made of textured rubber.

3. The medical system of claim 1, wherein the shield is made of latex.

4. The medical system of claim 1, wherein the shield covers a portion of the briefs.

5. The medical system of claim 1, wherein said pouch has an opening that allows the hollow tubular device to be inserted and stored therein.

* * * * *